United States Patent [19]

Uhlin et al.

[11] Patent Number: 4,495,287

[45] Date of Patent: Jan. 22, 1985

[54] PROCESS FOR PRODUCING GENE PRODUCTS OF PLASMID HAVING TEMPERATURE DEPENDENT PLASMID COPY NUMBER

[75] Inventors: Bernt E. Uhlin; Kurt Nordström; Soeren Molin, all of Odense, Denmark

[73] Assignee: A/S Alfred Benzon, Copenhagen, Denmark

[21] Appl. No.: 908,108

[22] Filed: May 22, 1978

[30] Foreign Application Priority Data

Dec. 30, 1977 [DE] Fed. Rep. of Germany ....... 2759053

[51] Int. Cl.$^3$ ..................... C12N 9/86; C12N 15/00; C12N 1/00; C12P 21/00
[52] U.S. Cl. ................................ 435/231; 435/172.3; 435/68; 435/317; 435/820; 935/27; 935/43; 935/60; 935/73
[58] Field of Search .................. 435/172, 317, 231, 68

[56] References Cited

U.S. PATENT DOCUMENTS 4,237,224  12/1980  Cohen et al. ....................... 435/172

OTHER PUBLICATIONS

Nordstroem et al., Proc. Soc. Gen. Microbiol., vol. 2, pp. 37 & 38, (1975).
Hashimoto-Gotoh et al., J. Bacteriology, vol. 131, No. 2, pp. 405-412, Aug. 1977.
Goebel, Eur. J. Biochem., vol. 43, pp. 125-130, 1974.
Lewin, Gene Expression, vol. 3, Plasmids and Phages, John Wiley & Sons, pp. 266-273, (1977).
Nordstroem et al., Microbiology, pp. 92-95, (1978).
Chemical Abstracts, vol. 88, 133092v, (1978).
Chemical Abstracts, vol. 89, 159981e, (1978).
Chemical Abstracts, vol. 83, 144393s, (1975).
Chemical Abstracts, vol. 84, 176581p, (1976).
Uhlin et al., Molec. Gen. Genet., 165, pp. 167-179, (1978).
Plasmid, vol. 1, pp. 1 to 7 and 117, (1977).
Chemical Abstracts, vol. 88, 166395z, Top Intect. Dis., pp. 299-332, (1977).
Abstract entitled "A Mutant Plasmid with Altered Replication Control", by Grindley et al., distributed at Second ASM Meeting on Extrachromosomal Elements, Jackson, Wyoming, 2/20-25/77, No. 5.
Microbiology-1978, Edited by David Schlesinger, 1978, pp. 71-73.
Abstract Distributed at Workshop on Plasmids and Genetic E Change Between Bacteria, Berlin, May 22-25, 1976.
Abstract entitled "Control of Plasmid R1 Replication in *Escherichia Coli:* Genetics, Selection, Timing and Control Parameters", by Nordstrom et al., distributed at Second ASM Meeting on Extrachromosomal Elements, Jackson, Wyoming, 2/20-25, 1977, No. 1.
*Topics in Infectious Diseases*, vol. 2, R-Factors: Their Properties and Possible Control, "Copy Mutants of the Plasmid R1 as a Tool in Studies of Control of Plasmid Replication", Nordstrom et al., pp. 299-332.
Excerpts from Petter Gustafsson's doctroal thesis, May 27, 1977, pp. 29, 31, 8 and 9.
Abstract distributed at FEMS Meeting in Paris, Dec. 1-2, 1976, entitled "Replication Control: Copy Mutants of Plasmids", Nordstrom et al.
Abstract distributed at Symposium about R factors in Tokyo, Japan, Oct. 26-28, 1977, entitled "Replication and Copy Number Control of the R Plasmid R1 in *E. Coli*", Uhlin et al.
*Journal of Bacteriology*, "Cold-Sensitive Mutations in *Salmonella Typhimurium* Which Affect Ribosome Synthesis", by Tai et al., Mar. '69, pp. 1298-1304.

(List continued on next page.)

*Primary Examiner*—Alvin E. Tanenholtz
*Attorney, Agent, or Firm*—Hubbell, Cohen, Stiefel & Gross

[57] ABSTRACT

Gene products of plasmid DNA, such as proteins, are prepared in high yields by cultivating bacteria carrying a plasmid which shows a controlled constant plasmid copy number at one temperture and a much higher or totally uncontrolled copy number at a different temperature. The plasmid may be prepared by recombinant DNA technique using a cloning vector showing the temperature dependent plasmid copy number pattern.

10 Claims, 4 Drawing Figures

PROCESS FOR PRODUCING GENE PRODUCTS OF PLASMID HAVING TEMPERATURE DEPENDENT PLASMID COPY NUMBER

FIELD OF THE INVENTION

The present invention provides a process for producing a gene product of plasmid DNA, to bacteria and plasmids useful in the process, to a cloning vector which can be used in constructing recombinant DNA plasmids useful in the process, and to a method of preparing such bacteria, plasmids, and cloning vectors.

BACKGROUND OF THE INVENTION

It is known to prepare useful polypeptides and proteins, for example enzymes, hormones, and (for use in e.g. vaccine preparation) toxins and other antigens, by cultivation of bacteria carrying plasmids with genes coding for the desired polypeptides or proteins. It is also known to construct plasmids containing desired genes by so-called recombinant DNA technique, which makes it possible to obtain, from the cultivated bacteria carrying such recombinant DNA plasmids, gene products which inherently are characteristic to other organisms than the bacteria used as host cells. In the preparation of recombinant DNA, a so-called cloning vector, that is, a plasmid which is able to replicate in the host bacterium, is combined with a DNA fragment containing a gene or genes coding for the desired product or products.

The recombinant DNA technique, in its most useful form, is based on the following principle:

DNA can be cut into pieces in a very specific way by restriction endonucleases. These pieces can then be joined to each other by DNA ligase. DNA cloning utilizes a plasmid vector that is a circular DNA molecule containing only one site for one or several restriction endonucleases. Treatment of such a vector with a restriction enzyme gives one species of a linear molecule. If this molecule is mixed with a DNA sample that is also treated with the same endonuclease, it is possible by ligation to obtain molecules composed of the vector to which a foreign DNA fragment has been fused. These plasmid molecules are called recombinant DNA. The vector with the foreign DNA can be transformed into a bacterial host cell, which means that it is taken up by and replicated in the bacterial host. Since the vector is able to replicate, the foreign DNA is also replicated.

If the foreign DNA is transcribed and translated in the bacterial host, the gene products of the foreign DNA are produced in the bacterial host. This production is in general proportional to the gene concentration which, on its side is proportional to the number of copies of the recombinant DNA plasmid molecules per cell. This means that in order to obtain large quantities of the desired gene products of the plasmid, a high number of copies of the plasmid per bacterial cell should be aimed at. It is known that some cloning vectors inherently replicate in a high copy number per bacterial cell, up to about 100. However, if the gene product produced by the foreign DNA combined with such cloning vector is one which is not well tolerated by the bacterial host, there may be difficulties in propagating a bacterial clone up to the desired production size culture because of inhibition exerted by the gene product. On the other hand, even a copy number of the order of about 20–100 will not always give rise to satisfactory yield of the desired gene product in the production culture. It is known that the number of copies of plasmids can be further increased by amplifying the inhibition of the protein synthesis, for example by addition of chloramphenicol, but as protein synthesis is necessary for preparing gene products of the cloned DNA, the amplified DNA will only be useful for formation of gene products thereof if the protein synthesis inhibiting component can be removed again, which is not always possible and often a complicated procedure.

DETAILED DESCRIPTION OF THE INVENTION

The present invention provides a process for preparing a gene product of a DNA plasmid, in which the plasmid is one which allows both effective plasmid amplification and obtainment of large quantities of the plasmid gene products. The invention utilizes plasmids having a temperature-dependent plasmid copy number pattern in that the plasmid shows a controlled constant plasmid copy number when host bacteria carrying the plasmid are cultivated at one temperature, but which plasmid shows, when the host bacteria carrying the plasmid are grown at a different temperature, an altered plasmid copy number pattern allowing a much higher or totally uncontrolled copy number. Hence, the number of copies of such plasmid is low at one temperature, which is an advantage since it decreases the risk that the cloned plasmid or its gene products should disturb growth of the host bacterium. However, the amount of the plasmid can be rapidly increased by a simple temperature shift, whereby simultaneous formation of the cloned plasmid and its gene products is obtained, and the production of gene products of the plasmid proceeds rapidly.

In accordance with this, the invention provides a process for producing a gene product of plasmid DNA, said process comprising cultivating bacteria carrying a plasmid showing a controlled constant plasmid copy number when the host bacteria are cultivated at one temperature, and showing, when the host bacteria carrying the plasmid are grown at a different temperature, an altered plasmid copy number control allowing a much higher or totally uncontrolled copy number; under conditions including at least a period of cultivation at or approaching a temperature at which the plasmid shows an altered copy number control allowing a much higher or totally uncontrolled copy number; and harvesting, from the bacterial culture, a gene product of the plasmid.

The crux of the present invention is the utilization of the particular type of plasmid having the temperature-conditioned plasmid copy number pattern and the recognition that this type of plasmid, when copied in a very high number at one temperature, also gives rise to production of large amounts of its gene products. The cultivation per se is suitably performed using conventional techniques, including conventional nutrient media which are known to be optimal to the bacterial species in question, and also, the harvesting of the gene products is performed in accordance with well-known methods adapted to the identity and properties of the particular gene product prepared, the properties of the host bacteria, etc. Special and critical to the process of the present invention is the temperature regulation involving at least a period of cultivation at or approaching a temperature at which the plasmid shows an altered copy number pattern allowing a much higher or totally uncontrolled copy number, in other words, involving a period of cultivation during which the plasmid is copied in a high number of copies, and, as it has been found, during which gene products of the plasmid are formed in correspondingly high amounts.

The plasmid having temperature-dependent plasmid copy number pattern may be one prepared by recombinant DNA technique using a cloning vector showing the temperature-dependent copy number pattern, or the plasmid may be one obtained by mutagenization of an existing plasmid having genes for a desired production.

A detailed description of plasmids showing the above-mentioned temperature-dependent plasmid copy number pattern has not been given previously and appears from the below examples which describe the preparation of some plasmids of this kind, including plasmids useful as cloning vectors.

The plasmid showing the above-mentioned temperature-dependent plasmid copy number pattern with controlled constant copy number per cell at one temperature and a much higher or totally uncontrolled copy number (in the following often termed "runaway-replication") at another temperature may be prepared by mutagenization of an existing plasmid which is known to replicate autonomously in the host bacterium in question. In accordance with known principles, the mutagenic treatment can be performed in vivo or in vitro, and while the mutagenic agents so far used appear from the examples, it is assumed that the kind of mutagenic treatment is not critical. After the mutagenic treatment (and, if the mutagenic treatment was performed in vitro, transformation of the mutagenized material into the host bacterium), a bacterial clone in which the plasmid copy number is controlled when the bacteria are cultivated at one temperature and in which the plasmid copy number is much higher or totally uncontrolled when the bacteria are grown under different temperature is then to be isolated. The isolation procedure may be based upon screening at two temperatures between which a shift in plasmid number copy control pattern is sought for. One indication useful in such screening is the fact that on a substrate which is known to be non-limiting to the host bacterium in question, growth inhibition especially at a particular temperature is likely to be due to the production of a large number of copies of plasmid and/or of large amounts of gene products thereof.

It has been found that a more suitable way of isolating a plasmid mutant showing runaway-replication pattern is often to use a two-stage mutagenic treatment comprising a first stage in which a plasmid-carrying bacterial clone is isolated in which the plasmid shows one plasmid copy number control pattern at one temperature and another plasmid copy number control pattern permitting a higher copy number at a different temperature, and a second stage to obtain, from the mutant obtained from the first stage, a plasmid-carrying bacterial clone in which the plasmid shows a much higher or totally uncontrolled copy number at said second (different) temperature. This procedure allows optimum utilization of suitable selection techniques, for example double antibiotic selection:

One type of plasmid copy mutants has the following characteristics: At low temperature (e.g. 30° C.), the copy number is close to that of the parent plasmid, while at higher temperature (e.g. 40° C.), the copy number is about 4-fold higher. A suitable isolation procedure used to isolate such mutants makes use of the fact that the resistance towards ampicillin and chloramphenicol is directly proportional to the concentration of genes coding for the corresponding resistance enzymes (Uhlin et Nordström, Plasmid 1, 1977), and of the fact that ampicillin kills only bacteria which are in a phase of growing.

It has been found that strains containing plasmid R1drd-19 (which is described in greater detail below) exhibit a single cell resistance on LA plates of about 100 μg ampicillin/ml and of about 100 μg chloramphenicol/ml. The resistance in liquid medium towards these two antibiotics is about the same as on LA plates. The resistance towards ampicillin and chloramphenicol is directly proportional to the gene concentration (Uhlin et Nordström, Plasmid 1, 1977). This effect has been used to isolate mutants of plasmid R1drd-19 with an increased copy number, so-called copy mutants. However, the combination of a bacteriostatic and a bacteriocide can also be used to isolate copy mutants with different copy numbers at different temperatures, as this selection method allows easy counter-selection of both parent plasmid and non-conditional copy mutants. The following procedure was found to be a suitable one: It is assumed that a copy mutant exists with a low copy number at a low temperature (30° C.) and a high copy number at a high temperature (40° C.) (the procedure is, however, not limited to this type of copy mutant, but can also be used to isolate other possible types of temperature-dependent copy mutants).

The culture of the plasmid-containing cells is grown at 30° C., and chloramphenicol is added to a concentration (300 μg/ml) which inhibits the growth of cells containing plasmids with normal copy number. The cells containing plasmids with a high copy number at 30° C. are killed with ampicillin (4000 μg/ml). The surviving cells are collected and the temperature is raised to 40° C. Cells containing plasmids with a high copy number at 40° C. are selected on ampicillin plates (500–2000 μg/ml). Among the cells surviving, some should contain temperature-dependent plasmid copy mutants.

Cells selected in the above manner can then be subjected to further mutagenic treatment, and a suitable method for selecting, among the thus mutagenized cells, a mutant having runaway behaviour at the second temperature has been found to comprise an initial selection for cells which, at the lower temperature, show a controlled and constant, but increased copy number, indicating that the replication control system has again been subject to mutation.

The particular type of mutation which has occurred in the specific plasmids illustrated in the examples is not yet known with certainty, but it is believed that an effect of the mutation is that a protein mediated by the plasmid and involved in the plasmid copy number control has, due to the mutation, become modified into a form which is not stable at the higher temperature. While it is evident that the most practical embodiment of the plasmid of the invention, when it is to be used as a cloning vector, is one which, like the cloning vectors described in the examples, in itself contains all elements necessary for the temperature-dependent copy number behaviour, it is also obvious that the principles of the present invention and advantages conferred thereby may also manifest themselves when the mutation is of the nonsense type combined with corresponding temperature-dependent nonsense suppressor in the host bacterium, for example when the plasmid is an amber mutant and the host bacterium is one which shows temperature-dependent amber suppressor effect.

The temperature at which the plasmid shows runaway behaviour will not necessarily be one which is higher than the temperature at which the plasmid shows a controlled constant copy number, also the reverse situation is possible. If it is desired to prepare a mutant showing runaway replication at a lower temperature than the temperature giving controlled constant copy number, the selection or screening criteria are adapted correspondingly. However, when the gene product to be prepared by cultivating the plasmid-containing bacteria is one which is not deteriorated at the higher temperature, it is preferred that the temperature at which the plasmid shows runaway replication is a higher temperature than the one giving a controlled constant plasmid copy number. When this applies, the amplification of the plasmid takes place under the same conditions allowing the relatively highest cell growth rate. The plasmids illustrated in the working examples were designed to show, in the mesophilic bacteria exemplified by Escherichia coli, a constant controlled plasmid copy number at 30° C., and runaway behaviour at 40° C. As will appear from the data on these plasmids, the constant controlled plasmid copy number is retained up to about 32° C. for these plasmids and the temperature at which the plasmid shows runaway behaviour is above about 36° C. The most interesting plasmids of the present invention are plasmids which show a reasonably large, but constant copy number at one temperature, and a copy number which is at least 20 times higher at the different temperature. Whether or not total runaway behaviour with resulting death of the cell is obtained will to some extent depend upon the bacterial host and its ability to tolerate the plasmid and its gene products in high concentration.

Hence, the present invention permits, on the one hand, obtainment of plasmid copy numbers which were hitherto unobtainable, up to the order of several thousand per cell, and, as it has been found, concomitant high production of gene products of the plasmid during a sufficient number of generations (usually 4–6) of growth at the high copy number to secure a considerable production of gene products. On the other hand, the invention provides a most simple control of the copy number, which may be utilized in various manners, depending upon the individual conditions with respect to bacterial host, desired gene product, etc.: In most cases, it will be preferred that the propagation of the bacteria from an individuum or a clone up to a production size culture is performed at or near the temperature at which the plasmid shows a controlled constant copy number, in order to avoid any inhibition of the bacterial growth by an increasing plasmid and gene product concentration. Thereafter, the temperature may be shifted to a temperature at which the plasmid shows an altered copy number control allowing a much higher or totally uncontrolled copy number, and after a suitable production period, often until the growth of the bacteria is inhibited by the production of the plasmid and/or gene products thereof, the harvesting of the gene product is performed. Depending on the particular conditions, it may be desired to perform the production cultivation at a temperature which is only approaching the temperature at which the plasmid shows the altered copy number control, so as to obtain a steady-state culture giving a high yield of gene product (which may then be continuously or intermittently harvested from the culture in a manner known per se), but at which temperature the host cells survive and are still capable of propagation.

One example of the unique control possibilities obtained through the present invention is preparation of a temperature-sensitive protein as the desired gene product. In such case, the bacterium may be propagated up to production size culture at the temperature at which the plasmid copy number is controlled and constant, and thereafter, by a temperature shift to the runaway temperature, the plasmids may be amplified. Subsequent to amplification of the plasmids and while the cells are still viable and capable of propagation, the temperature is again shifted to the lower temperature giving constant copy number, and at this lower temperature, the resulting bacteria carrying the much higher number of plasmids per cell are used for the production of the temperature-sensitive protein in question. It is known that there are many organisms which are not viable at temperatures above about 30° C., and the proteins of which, therefore, may be denatured at higher temperatures. Therefore, this embodiment of the temperature regulation may prove especially important when gene products inherent to such organisms are to be prepared by recombinant DNA/cloning technique.

As indicated above, the plasmid showing the characteristic temperature-dependent copy number behaviour involving runaway replication may be one derived by mutagenic treatment, from a parent plasmid possessing genes for the desired production, but without the characteristic runaway behaviour. However, for many practical purposes the plasmid used in the production cultivation will be one prepared by recombinant DNA technique, using as a cloning vector a suitable plasmid showing the characteristic temperature-dependent runaway replication. This combines the advantages of the conventional recombinant DNA technique with the advantages of the temperature control and the very high obtainable number of plasmid copies per cell, with the consequent amplified production of polypeptide or protein mediated by the foreign DNA fragment. It is contemplated that the very high number of plasmid copies obtainable by using a cloning vector of the present invention will permit production of large or at any rate reasonable amounts of proteins which, due to their being genetically relatively remote from the host bacterium in question, could hitherto not be produced at all, or at any rate not be produced in a satisfactory amount, by cloning techniques. Hence, the cloning vector aspect of the present invention is a very important aspect.

In order to be useful as a cloning vector, the plasmid should show, for at least one restriction endonuclease, one and only one site susceptible to the endonuclease, and the said site should be one which after insertion of a fragment of foreign DNA at this site, permits the resulting recombinant DNA to replicate autonomously and, to obtain the advantages of the present invention, with retention of the capability of showing the temperature-dependent copy number pattern.

The most suitable restriction endonucleases for use in recombinant DNA technique are those giving the so-called "cohesive ends" on both the cloning vector and the DNA fragment, in other words, single stranded regions at the ends of the molecules with complementary base sequence allowing base pairing to identical sequences.

As appears from the examples, cloning vectors having one site for restriction endonuclease have been prepared, and also vectors having one site for one restriction endonuclease, and another site for another restriction endonuclease, has been prepared. An advantageous way of constructing cloning vectors fulfilling the above conditions is often to prepare, from a larger plasmid showing the temperature-dependent runaway replication, a "miniplasmid" of sufficiently small size to show only one site susceptible to a useful restriction endonuclease, but with sufficient size to still contain the genes indispensable to the special temperature-dependent replication behaviour. Such miniplasmids may be prepared from a larger plasmid by isolating bacterial clones carrying either spontaneously occurring or in vitro—prepared (and thereafter transformed) miniplasmid derivatives of the parent plasmid. The isolation of the desired miniplasmids (or bacteria containing them) is performed by suitable and well-known screening and/or selection methods.

In principle, an ideal cloning vector is one which contains as few genes as possible coding for the production of non-desired proteins. However, for many purposes, it is desired that the cloning vector contains genes mediating a so-called marker useful for identification and/or selection of cells carrying the plasmid. The most useful marker is antibiotic resistance, for example ampicillin resistance, as this permits, after a treatment for transforming a recombinant DNA into a bacterial host, an easy counter-selection of bacteria which have not received the recombinant plasmid. However, also cloning vectors without a marker may be useful cloning vectors, for example when the genes to be inserted by the recombination in themselves carry a marker.

When it is desired to introduce a marker, for example antibiotic resistance, in a plasmid of the present invention to be used as a cloning vector, this may be done by transposition of a DNA fragment in a manner known per se. An example of such transposition is illustrated in Example 5. Another way of introducing a foreign DNA fragment mediating a marker function would be by recombinant DNA technique, but this would consume a restriction site on the cloning vector and can, therefore, only be used in the cases where the cloning vector has at least two restriction sites useful in recombinant DNA technique.

Another embodiment of the preparation of a cloning vector of the present invention is to introduce, by mutagenization, the above-described temperature-dependent runaway replication in an existing cloning vector known to function well in a desired organism, for example the plasmid pSC101 which is a well-established cloning vector in E. coli.

Methods used in the Examples

Several Escherichia coli K-12 stains (Table 1) and plasmids (Table 2) were used.

The experimental techniques used were standard techniques used in microbial genetics (J. Miller, Methods in Molecular Biology, Cold Spring Harbor Laboratory) and in genetic engineering (T. Tanaka and B. Weissblum, J. Bacteriol. 212 (1975) 354–362).

TABLE 1

| Strain | Genotype | Reference or Source |
|---|---|---|
| \multicolumn{3}{l}{Escherichia coli K-12 strains} | | |
| EC1005 | thi, met, nal, relA | Grindsted et al, J. Bact. 110 (1972) 529. |
| D11 | thi, his, pro, trp, strA | Boman et al, Genet. Res. 12 (1968) 169. |
| C600 | thi, lac, leu, thr | Appleyard, R. K., Genetics 39 (1954) 440. |
| UB1731 | thi, met, pro, amp (Tn 802), nal | Bennett, P. M. and M. H. Richmond, J. Bact. 126 (1976) 1. |
| 1100 | thi, endoI | |

TABLE 2

| Plasmid | Source |
|---|---|
| Rldrd-19 | Meynell & Datta, Nature 214 (1967) 885. |
| pSF2124 | So et al, Molec. gen. Genet. 142 (1975) 239. |

Plasmid R1 is a transferable plasmid that mediates resistance to the following antibiotics: ampicillin, chloramphenicol, kanamycin, streptomycin, and sulphonamides. The plasmid has a molecular weight of $65 \times 10^6$ daltons. Normally, in Escherichia coli, the plasmid is present in about one copy per chromosome equivalent. It is possible by mutation in this plasmid to increase the copy number several fold above this level, so-called copy mutants (K. Nordström et al., J. Bacteriol. 110, 562–569 (1972)).

In the examples, the following stages are described:
Example 1: Isolation of a plasmid mutant (pKN301) which has a temperature-dependent replication control. The copy number of this plasmid increases about 4 fold at higher temperature.
Example 2: The isolation from plasmid pKN301 of a mutant (pKN400) that lacks replication control at higher temperature (a runaway mutant).
Example 3: The isolation from plasmid pKN400 of a miniplasmid (pKN402) that retains the runaway behaviour but carries only one site for the restriction endonuclease EcoR1.
Example 4: The isolation from a derivative of plasmid pKN400 of another miniplasmid that retains the runaway bahaviour but carries only one site for the restriction endonuclease EcoR1.
Example 5: The insertion, by translocation, of an antibiotic resistance marker into miniplasmid pKN402 to obtain miniplasmid pKN403.
Example 6: Insertion of a Streptomycin resistance gene on miniplasmid pKN403 and cloning.

BRIEF DESCRIPTION OF THE DRAWINGS

FIG. 1a: The amount of covalently closed circular (ccc) DNA was analysed by ethidium bromide-cesium chloride gradient centrifugation after labelling with $^3$H-thymidine. The plasmid DNA content was calculated as % of chromosomal DNA.
FIG. 1b: The total amount of DNA and protein of the cells was measured chemically and the ratio DNA/protein is shown in a relative scale with the value for strain D11-R1drd-19 at 30° C. set for 100%.

FIG. 1c: Growth rate (doublings/hour) was determined by measuring the optical density in a Klett-Summerson colorimeter.

FIG. 3a shows the result after logarithmic growth at 30° C. and

FIG. 3b shows the result after 3 hours of growth at 40° C. The density of the gradients is increasing from right to left and the total number of fractions was 63 (FIG. 3a) and 52 (FIG. 3b), respectively.

EXAMPLE 1

A 40 ml culture of strain EC1005 containing the plasmid R1drd-19 was grown at 30° C. in casamino acids medium. At a cell density of about $10^8$ cells/ml the cells were chilled and harvested by centrifugation at 4° C. The cells were washed once in isotonic NaCl solution, resuspended in 1M hydroxylaminehydrochloride (pH 6.0), and incubated at 37° C. for 20 min. After the mutagenization the culture was cleared of the mutagen and diluted in LB medium (30° C.) to a cell density of about $10^7$ cells/ml. This culture was divided into 4 aliquots and incubation was continued at 30° C. After 60 min. at 30° C. chloramphenicol (300 µg/ml) was added and 10 min. later ampicillin (4000 µg/ml). Incubation was continued for another 60 min.. The surviving cells were harvested, washed twice with LB medium (40° C.) and resuspended in LB medium (40° C.) to a cell density of about $5 \times 10^8$ cells/ml. The cultures were incubated for 30 min. at 40° C. and the cells in the cultures were then plated on LA plates containing different concentrations of ampicillin (300–2000 µg/ml). The plates were incubated over night at 40° C. and the surviving colonies isolated and tested for their resistance pattern at 30° C. and 40° C. Cells possessing an ampicillin resistance of at least 500 µg/ml at 40° C. were found with a frequency of $10^{-6}$. Four hundred colonies isolated from 500–2000 µg ampicillin/ml were picked, subcultured and tested for temperature-dependent resistance. Five clones, 4 of them from individual subcultures, showed more than a 3-fold difference in resistance between 30° C. and 40° C. After transfer of the plasmids to an unmutagenized strain EC1005, resistance to ampicillin, streptomycin and chloramphenicol was determined. All 5 clones showed a 3–5-fold increased resistance to all three antibiotics at 40° C. compared to 30° C. (The parent plasmid exhibited resistances of 75 and 125 µg ampicillin/ml at 30° C. and 40° C., respectively). One of the mutants, pKN301, was analyzed in greater detail. This plasmid has the same molecular weight as the parent plasmid, R1drd-19 ($65 \times 10^6$ daltons).

COPY NUMBER ANALYSIS OF PLASMID pKN301

Plasmid content was measured in two ways, by determination of CCC-DNA and of specific activity of $\beta$-lactamase. The amount of CCC-DNA for each plasmid under different growth conditions was measured both as the amount of fast-sedimenting material in an alkaline sucrose gradient and as the amount of satellite band in a dye-CsCl buoyant density gradient (Table 3). The mutant, when grown at high temperature, showed 3 to 4 times as much plasmid DNA as the same bacterium carrying plasmid R1drd-19, while at low temperature the amount of plasmid DNA was close to that of the parent plasmid.

TABLE 3

| Plasmid copy number of cells carrying plasmid pKN301 at different temperatures[a] | |
|---|---|
| Temperature (°C.) | Copy number[b] pKN301 |
| 30 | 1.2 |
| 34 | 1.3 |
| 35 | 1.7 |
| 37 | 4.0 |
| 39 | 4.1 |
| 40 | 3.4 |
| 44 | 3.7 |

[a]in EC1005 was used as host.
[b]Copy number was ascertained by determining the CCC-DNA/chromosomal DNA ratio on dye/CsCl density gradients. Values are given relative to parent plasmid R1drd-19, which is set to 1.0 at each temperature.

EXAMPLE 2

Isolation of a runaway-replication plasmid mutant (pKN400)

Figure 1:
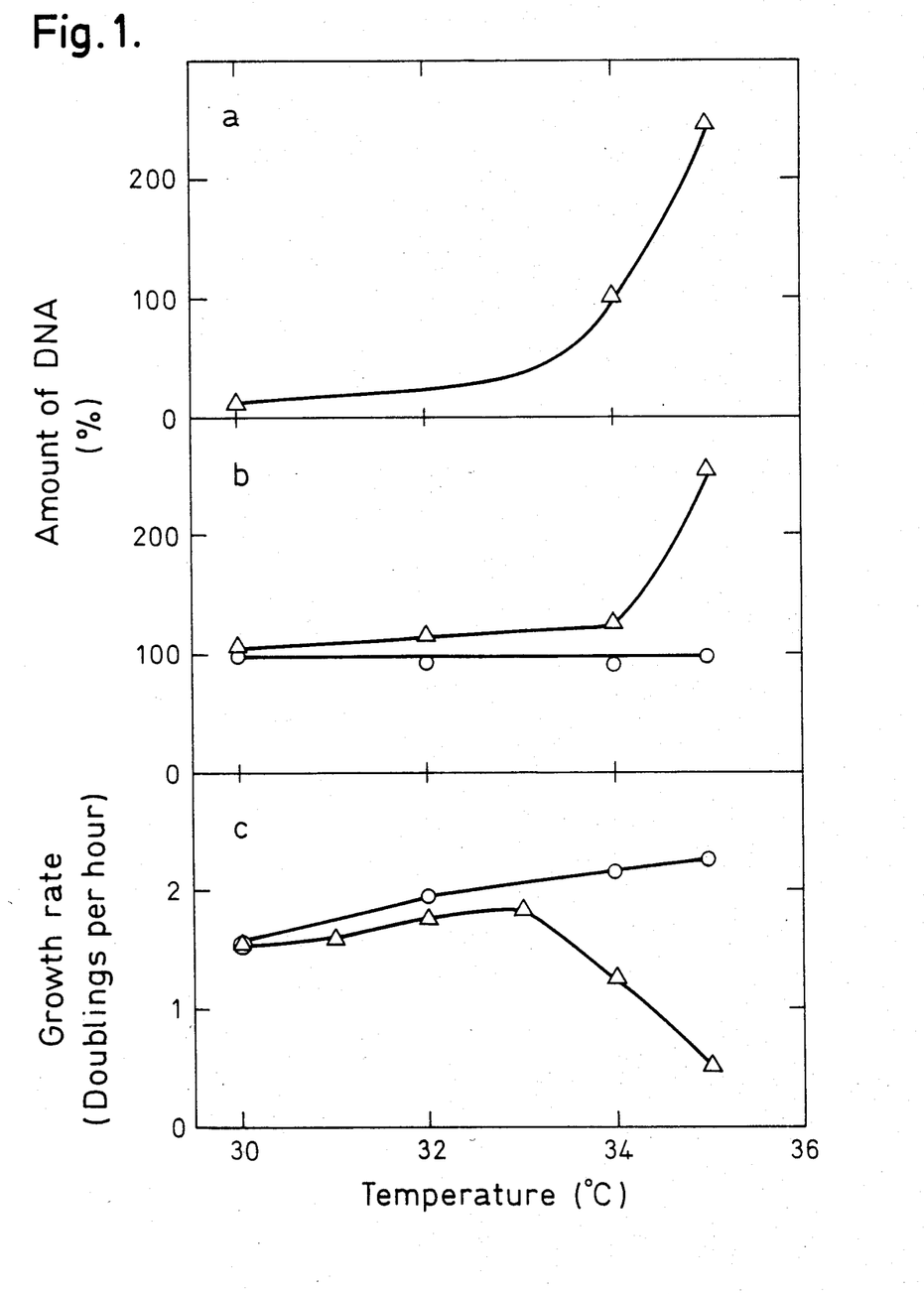
FIG. 1 shows the properties of a runaway-replication plasmid mutant. Strain D11 carrying plasmid R1drd-19 (o) or pKN400 (Δ) was grown logarithmically in LB medium at different temperatures.
Figure 2:
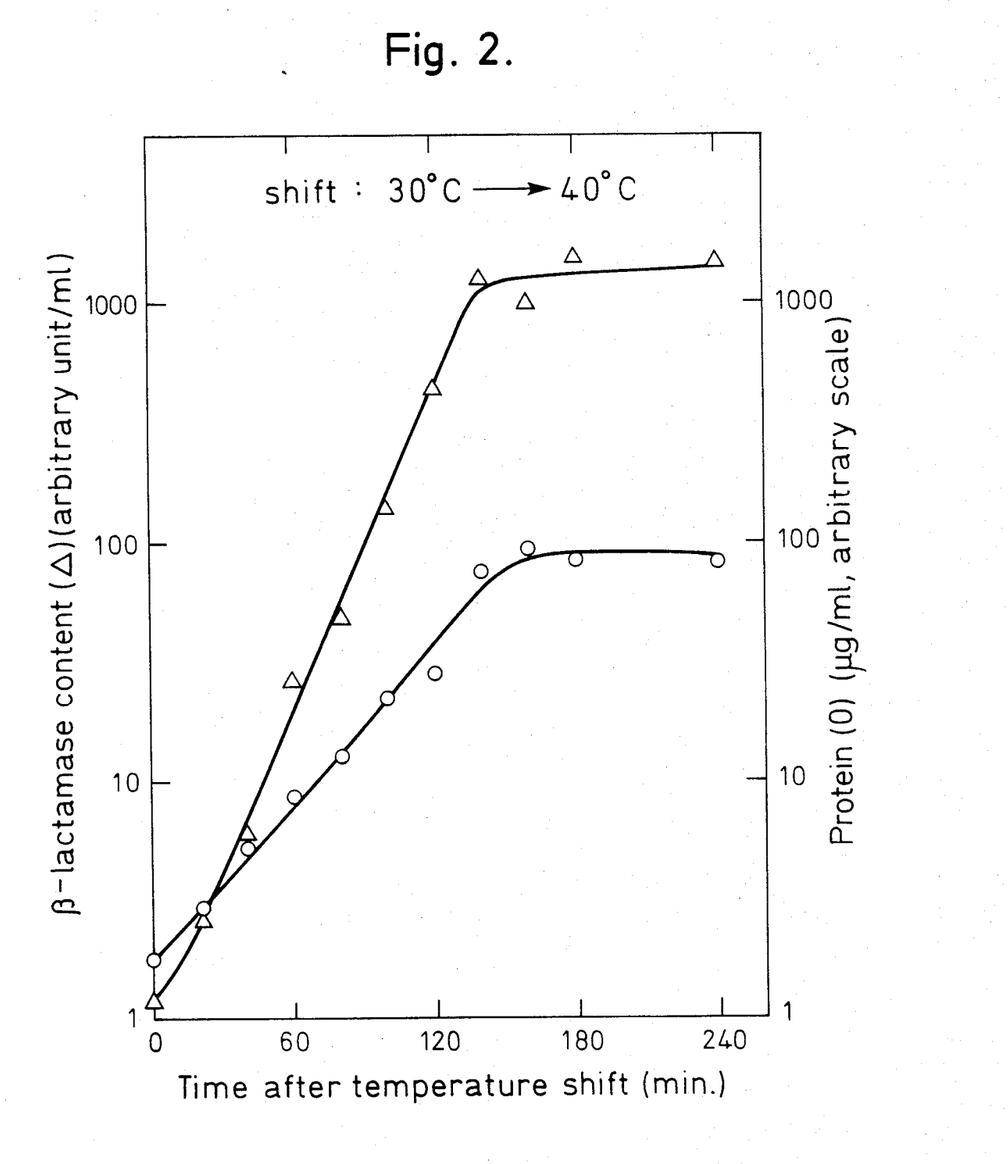
FIG. 2 shows the relative increase in plasmid mediated $\beta$-lactamase content and total protein of strain D11-pKN400 at 40° C. A culture growing logarithmically in LB-medium at 30° C. was shifted to 40° C. During the subsequent growth, samples were taken and assayed for amount of $\beta$-lactamase and total protein. The relative increase after the temperature shift is plotted on a logarithmic scale.

As described in Example 1, it is quite evident that when the mutation in plasmid pKN301 is expressed, the copy number is still carefully controlled. This temperature-dependent copy number mutant has been used as the parent plasmid in the search for plasmid mutants which have no control of the copy number at a condition where the mutation is expressed. A second mutation that affected the copy number level of pKN301 at 30° C. was introduced and then tests for the behaviour of the mutant at higher temperatures were carried out:

Strain 1005 carrying plasmid pKN301 was mutagenized with ethyl methane sulphonate and clones with increased resistance to ampicillin were selected on plates at 30° C. Then the clones were tested at different temperatures and some of the isolates were found to have a drastically reduced viability at 37° C. and 42° C. By transfer of the plasmid to an unmutagenized host strain by conjugation it was shown that the reduced viability was caused by the mutant plasmid. One of the isolates were chosen for further work. In the transfer to the unmutagenized host (strain D11) selection for the plasmid recipient was done by selecting cells resistant to chloramphenicol (25 µg/ml), and the recipient now carrying the plasmid was subsequently tested for the presence of other plasmid-mediated resistances. The plasmid of a clone that did show all R1-mediated resistances was denoted pKN400. Some of the properties of pKN400 in strain D11 are illustrated in FIG. 1, which summarizes the results after the cells were grown at different temperatures. There was a drastic increase in the amount of plasmid DNA at temperatures above 34° C. (FIG. 1a). A similar increase was shown for the total amount of DNA in the cells (FIG. 1b), and there was a corresponding decrease in the growth rate of the cells (FIG. 1c). The bacteria did not grow at a measurable rate at temperatures above 35° C. By shifting a culture growing at 30° C. to 37° C. (or 40° C.) it has been shown that at the higher temperature there is no copy number control left to regulate the plasmid replication. The plasmid copy number then increases logarithmically which eventually becomes lethal for the host cell. An important finding is that, during such a temperature shift, the plasmid genes are expressed throughout the entire period when the amount of plasmid increases. The resulting gene dosage effect is illustrated in FIG. 2, which shows the increase in total amount of protein and of the plasmid mediated $\beta$-lactamase.

EXAMPLE 3

A miniplasmid with temperature-dependent runaway-replication (pKN402)

Some years ago it was found that a plasmid copy mutant could spontaneously give rise to smaller plasmid segregants, miniplasmids, that were able to replicate automonously (Goebel and Bonewald, J. Bact. 123 (1975), 658–665. Later, a large number of such miniplasmids have been isolated from various copy mutants. Various sizes of miniplasmids have been obtained with molecular weights down to about $4 \times 10^6$ daltons. The runaway-replication mutant plasmid pKN400 was found to be a good source for the isolation of miniplasmids, especially if uncontrolled plasmid replication was allowed by growth of the host cells at high temperature.

Figure 3:
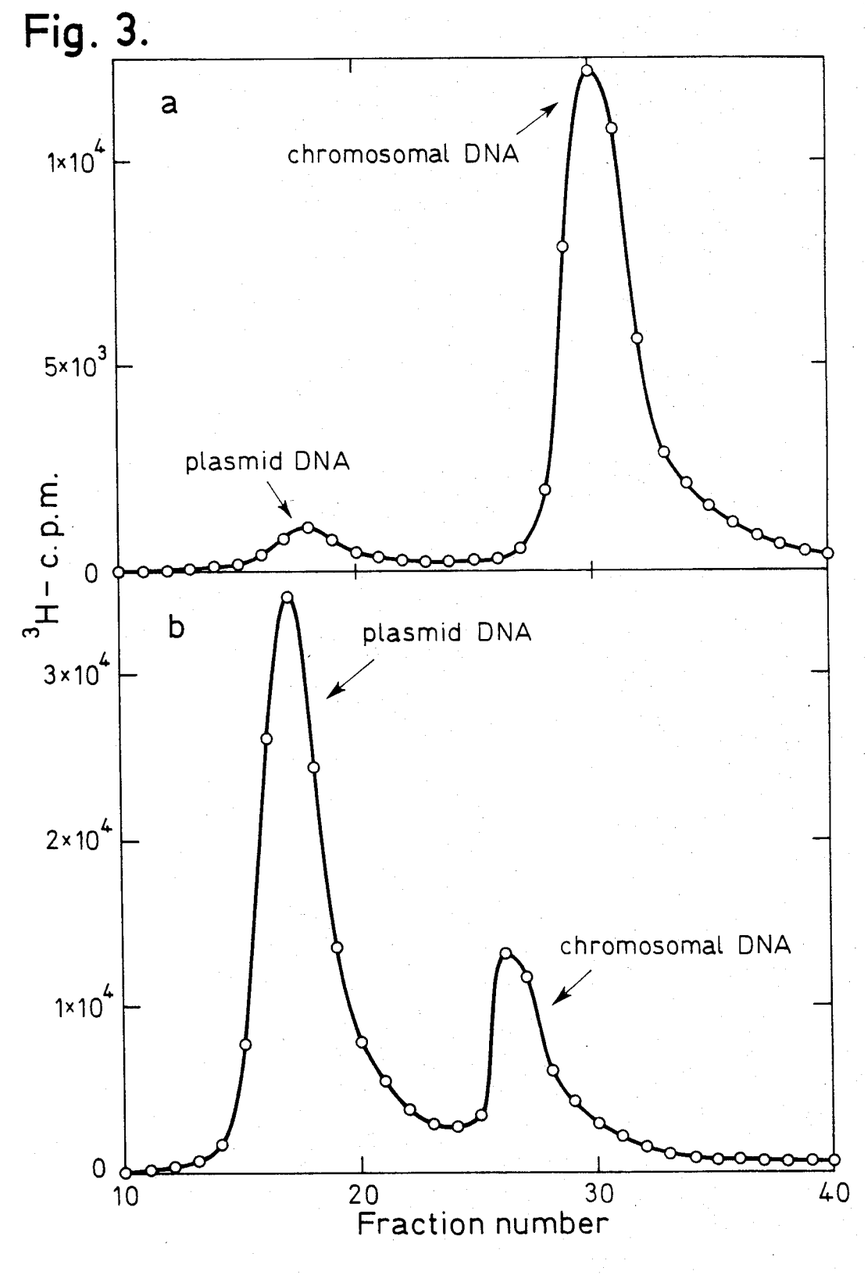
FIG. 3 shows the plasmid DNA content of strain C600-pKN402. Cultures of C600-pKN402, growing in LB-medium and labelled with $^3$H-thymidin, were analysed by cesium chloride-ethidium bromide centrifugation.

After a transfer of pKN400 to strain C600 some clones appeared to be very unstable with respect to plasmid maintenance as judged by tests (at 30° C.) for plasmid mediated antibiotic resistance. However, in some cases the temperature sensitive phenotype was retained although the cells no longer carried resistance to the antibiotics. By agarose gel-electrophoresis it was shown that these cells did carry a plasmid, and in all cases the molecular weight was about $5 \times 10^6$ daltons. One such clone was chosen for further work and the plasmid was denoted pKN402. Temperature shift experiments showed that this miniplasmid expressed the same temperature-dependent behaviour as the large plasmid (pKN400). The amount of plasmid DNA in strain C600/pKN402 was analyzed by cesium chloride-ethidium bromide density gradient centrifugation after growth at 30° C. (FIG. 3a) and after about 3 hours of growth at 40° C. (FIG. 3b). Since the molecular weight of pKN402 was estimated to be 4, $65 \times 10^6$ daltons it can be calculated that there are about 50 plasmid copies per cell at 30° C. and after the temperature shift the number increases to about 5000 copies per cell. For analysis with restriction endonucleases the DNA of pKN402 was purified by Ethidium Bromide/Cesium Chloride gradient centrifugation. It was found that digestion with the EcoR1 endonuclease yields one linear molecule; i.e. there is one site susceptible to the enzyme on pKN402 and that is a very important fact for the considerations of the usefulness of this plasmid as a cloning vehicle.

The strain E. coli K12 C600/pKN402 is deposited in the German Microorganism Collection (Deutsche Sammlung von Mikroorganismen, Grisebachstr. 8, D-3400 (Göttingen), hereinafter called DSM, under accession No. 1228.

EXAMPLE 4

Another miniplasmid with temperature-dependent runaway replication (pKN410)

Another miniplasmid derived from pKN401 (a derivative of pKN400, which has lost kanamycin-resistance) was isolated by an alternative method. Plasmid DNA (pKN401) was digested in vitro with the restriction enzyme EcoR1 and thereafter treated with the enzyme DNA ligase in order to fuse and seal the ends of the generated linear DNA fragments. The DNA was transformed to E. coli C600 cells and clones resistant to ampicillin were isolated and tester further. One of these clones having a phenotype similar to E. coli cells carrying the plasmid pKN401 (temperature sensitivity) was shown to carry a plasmid of the size $12 \times 10^6$ daltons (pKN410).

The copy number of this plasmid was found to be about 20 copies per cell at 30° C. and about 2000 copies per cell at temperatures above 37° C.

The presence of the ampicillin resistance gene on the plasmid was verified by transformation. Restriction enzyme analysis showed that pKN410 carried only one site susceptible to the restriction enzyme EcoR1, and only one site susceptible to the restriction enzyme BamH1.

Cultures of cells carrying pKN410 showed exactly the same growth pattern after a temperature shift from 30° C. to 40° C. as the parent plasmid pKN400, and there was a similar increase in the amount of the plasmid-mediated $\beta$-lactamase.

The strain E. coli K12 C600/pKN410 is deposited in the German Microorganism Collection (DSM) under accession No. 1230.

EXAMPLE 5

Introduction of an ampicillin resistance gene in miniplasmid pKN402 to obtain miniplasmid pKN403

The plasmid pKN402, though having the important properties of temperature dependent replication and the presence of a single site for the restriction enzyme EcoR1, does not possess a marker which can be used when selecting for bacterial clones harboring the plasmid. Since the step next to the in vitro joining of DNA fragments with the vector is a transformation of DNA to competent bacterial cells it is an advantage that transformed cells can be easily found. Therefore most cloning vectors carry an antibiotic resistance gene which enables cells having the vector to survive in a medium containing the corresponding antibiotic. A plasmid from pKN402 which carries the gene coding for $\beta$-lactamase, i.e. the cloning vector is resistant to penicillins, was prepared:

The first step in the construction of the penicillin resistant derivative of pKN402 was to bring the TnA transposon to the E. coli strain carrying pKN402. (For a description of transposons, consult Kleckner, Cell 11 (1977) 11–23).

This step was performed as a transduction with the bacteriophage P1. The strain E. coli K12, UB1731 carries the transposon Tn802 (TnA) on the bacterial chromosome.

A culture of this strain was infected with the bacteriophage P1 and a phage stock prepared. This P1-stock was used to transduce the strain C600/pKN402. The cells infected with P1 were spread on plates containing ampicillin (50 μg/ml). Colonies growing on these plates were purified and tested for ampicillin resistance and temperature sensitivity. (All methods are described in J. Miller: Methods in Molecular Biology). When Tn802 was inserted in the chromosome of E. coli, the cells became resistant to ca. 300 μg/ml benzylpenicillin. However, when the transposon is inserted in a multi copy plasmid the level of resistance is much higher. Therefore, there was selected for clones among the transduced C600/pKN402 that were resistant to 1000 μg/ml benzylpenicillin. Since pKN402 at 30° C. is present in ca. 50 copies per cell, it was expected that translocation of Tn802 to pKN402 would result in a higher level of penicillin resistance. 4 colonies of C600/pKN402 growing on 1000 μg/ml benzylpenicillin were selected for further analysis. When analysing the plasmid content of these 4 clones one had only one type of plasmid with a molecular weight of ca. $8 \times 10^6$.

(The insertion of Tn802 results in an increase of the molecular weight of the plasmid of $3.2 \times 10^6$). This clone was picked for further analysis and the plasmid termed pKN403. In order to verify that pKN403 had all the properties of pKN402 and in addition carried the Tn802 transposon, plasmid DNA was prepared from the strain C600/pKN403, and this DNA was transformed to another strain of E. coli K12. The transformed cells were grown on plates containing ampicillin (50 μg/ml), and a colony growing on such a plate was analyzed for the presence of the plasmid and for temperature sensitivity. It was found that the ampicillin resistant cells contained a plasmid of the same size as pKN403 and they were temperature sensitive. The DNA of pKN403 was analyzed with respect to the number of sites for the restriction enzymes EcoRl and BamHl and it was found that like pKN402 the plasmid pKN403 had only one EcoR1 site. In addition PKN403 carries one cut site for BamHl (presumably in the Tn802 sequence). Thus, at least two enzymes may be used when applying pKN403 as a cloning vector.

In shifts from 30° C. to 40° C. the cultures stops growing soon after. The copy number may be kept at a high steady-state level by using an intermediate temperature (e.g. 34° C.).

The strain E. coli K12 C600/pKN403 is deposited in the German Microorganism Collection (DSM) under accession No. 1229.

SUMMARY OF THE PROPERTIES OF THE TEMPERATURE-DEPENDENT CLONING VECTORS

The examples describe the isolation and characterization of 3 small plasmids which all may be used as cloning vectors.

One plasmid (pKN402) lacks any antibiotic resistance marker and may therefore be used when the DNA to be inserted in the vector has a genetic marker useful in selection, or when screening for plasmids with increased molecular weight is performed subsequent to the recombination. This vector may be very useful in the construction of other vectors, or in recombination with DNA carrying different genetic markers. In the plasmid pKN403 the presence of an ampicillin resistance gene makes a selection for plasmid carrying cells easy. Finally, the plasmid pKN410, carrying the ampicillin resistance gene, shows the growth characteristics of pKN400 after a temperature shift to 40° C. This plasmid is present in a low number per cell (20 copies/cell) at 30° C.

All the plasmids have one site susceptible to the restriction enzyme EcoR1.

EXAMPLE 6

Cloning of a streptomycin resistance gene on plasmid pKN403

Figure 4:
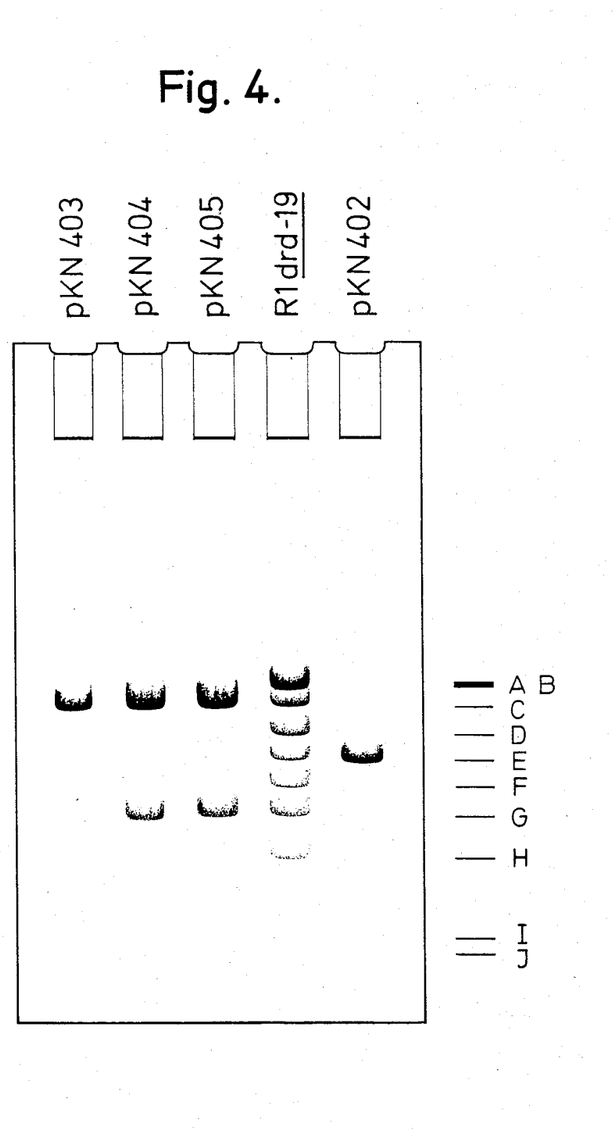
FIG. 4 shows EcoR1 restriction fragment analysis of in vitro constructed hybrid plasmids. Purified plasmid DNA was digested with EcoR1 endonuclease and the fragment pattern was analyzed by agarose-gel-electrophoresis. After staining in ethidium bromide solution, the gel was photographed under illumination of UV-light. From left the plasmids are: the cloning vehicle pKN403, two pKN403 based hybrid plasmids (pKN404, pKN405), the plasmid R1drd-19 as reference and plasmid pKN402 for comparison. The denotions of the EcoR1 fragments of R1drd-19 are shown to the right.

A cloning experiment was performed with the vector pKN403 in which an EcoR1 fragment carrying the gene mediating streptomycin resistance was inserted into the vector. A previously constructed hybrid plasmid consisting of the plasmid pSF2124 and the EcoR1 fragment G from plasmid R1drd-19 was used as the source of the streptomycin resistance gene. Purified DNA of the vector pKN403 and the mentioned hybrid plasmid was mixed and digested with the EcoR1 endonuclease in order to obtain linear fragments. The DNA was then treated with polynucleotide ligase and used in transformation of E. coli cells. Selection was made for cells having resistance to ampicillin and streptomycin at 30° C. Clones so obtained were tested for growth at 40° C. and most of them were found to be unable to grow at this temperature. Further analysis of such clones showed that they carry plasmids of exactly the molecular weight calculated for a hybrid plasmid consisting of plasmid pKN403 and the fragment G. FIG. 4 shows the EcoR1 fragment pattern of two such hybrid plasmids (pKN404, pKN405). It was also shown that the amplification of plasmid DNA at 37°-40° C. in case of pKN404 was similar to that found for pKN403.

It was therefore concluded that the insertion of a DNA fragment into the EcoR1 site of the vector thus constructing recombinant DNA molecules, does not alter the advantageous properties of the vector concerning amplification of DNA and/or gene products.

We claim:

1. A method for producing a gene product of DNA, comprising cultivating bacteria carrying a recombinant DNA plasmid showing a controlled constant plasmid copy number when the host bacteria are cultivated at one temperature, and showing, when the host bacteria carrying the plasmid are grown at a different temperature, an altered plasmid copy number control allowing an at least 20 times higher copy number, or a totally uncontrolled copy number under conditions including at least a period of cultivation at or approaching a temperature at which the plasmid shows an altered copy number control allowing an at least 20 times higher or totally uncontrolled copy number; said approaching temperature being a temperature at which the host bacteria survive and are still capable of propagation; and harvesting, from the bacterial culture, a gene product of the plasmid.

2. A method as claimed in claim 1 comprising performing cultivation at the temperature at which the plasmid shows a controlled constant copy number during seeding and multiplication stages and until an amount of cells sufficient for production size culture is obtained, and thereafter performing production comprising cultivation at or approaching the temperature at which the plasmid shows an altered copy number control allowing an at least 20 times higher or totally uncontrolled copy number, and harvesting.

3. A method as claimed in claim 1 wherein the cultivation at the temperature at which the plasmid shows an altered copy number control allowing an at least 20 times higher or totally uncontrolled copy number is continued until the growth of the bacteria is inhibited by the production of the plasmid or gene products thereof.

4. A method as claimed in claim 1, wherein the production scale cultivation is performed continuously at a temperature approaching the temperature at which the plasmid shows an altered copy number control allowing an at least 20 times higher or totally uncontrolled copy number so as to permit survival of the host cells concomitantly with formation of increased amounts of gene products of the plasmid, and wherein the gene product of the plasmid is continuously or intermittently harvested from the culture.

5. A method as claimed in claim 1, wherein the period of cultivation at or approaching a temperature at which the plasmid shows an altered copy number control allowing an at least 20 times higher or totally uncontrolled copy number is preceded by the propagation of the bacterial culture to reach production size culture, after the propagation the temperature is shifted to a temperature at or substantially at the temperature at which the plasmid shows an altered copy number control allowing an at least 20 times higher or totally uncontrolled copy number, and the temperature is maintained for a sufficient period to obtain a substantial amplification of the plasmid, but for a period sufficiently short to avoid any substantial impairment of the bacterial culture, whereafter the temperature is again shifted to a temperature at or approaching the temperature at which the plasmid shows a controlled constant plasmid copy number, and production cultivation of the culture having the amplified plasmid copy number is continued at said temperature at which the plasmid shows a controlled constant plasmid copy number.

6. A method as claimed in claim 1, wherein the temperature at which the plasmid shows an altered copy number control allowing an at least 20 times higher or totally uncontrolled copy number is higher than the temperature at which the plasmid shows a controlled constant plasmid copy number.

7. A method as claimed in claim 6, wherein the host bacteria are mesophilic bacteria, and wherein the temperature at which the plasmid shows a constant controlled plasmid copy number is up to about 32° C., whereas the temperature at which the plasmid shows an altered copy number control allowing an at least 20 times higher or totally uncontrolled copy number is above about 36° C.

8. A method as claimed in claim 1, wherein the plasmid is one prepared by combining a cloning vector with a foreign DNA fragment; said plasmid is a plasmid showing a controlled constant plasmid copy number when host bacteria carrying the plasmid are cultivated at one temperature, and showing when the host bacteria carrying the plasmid are grown at a different temperature, an altered plasmid copy number control allowing an at least 20 times higher or totally uncontrolled copy number; said cloning vector carrying for at least one restriction endonuclease, one and only one site susceptible to the endonuclease, said site being such that, after insertion of a fragment of foreign DNA at the site, the resulting recombinant DNA is able to replicate autonomously and with the retention of the capability of showing a controlled constant plasmid copy number when host bacteria carrying the recombinant DNA are cultivated at one temperature, and showing, when the host bacteria carrying the recombinant DNA are growing at a different temperature, an altered plasmid copy number control allowing an at least 20 times higher or totally uncontrolled copy number.

9. A method as claimed in any of claims 1–7, or 8, wherein said plasmid is a mini-plasmid.

10. A method as claimed in claim 1, wherein the plasmid is a derivative of R1.

* * * * *